US012702727B2

(12) United States Patent
Wu

(10) Patent No.: US 12,702,727 B2
(45) Date of Patent: Aug. 11, 2026

(54) THIN MAGNETIC ABSORPTION FRAGRANCE DEVICE

(71) Applicant: Blueprint Technology CO., LTD., Taipei City (TW)

(72) Inventor: Hua Ting Wu, Taipei City (TW)

(73) Assignee: Blueprint Technology CO., LTD., Taipei (TW)

(*) Notice: Subject to any disclaimer, the term of this patent is extended or adjusted under 35 U.S.C. 154(b) by 144 days.

(21) Appl. No.: 18/584,992

(22) Filed: Feb. 22, 2024

(65) Prior Publication Data

US 2025/0195710 A1 Jun. 19, 2025

(30) Foreign Application Priority Data

Dec. 14, 2023 (TW) ................................ 112213696

(51) Int. Cl.
*A61L 9/12* (2006.01)
*A61L 9/04* (2006.01)

(52) U.S. Cl.
CPC *A61L 9/12* (2013.01); *A61L 9/04* (2013.01); *A61L 9/127* (2013.01); *A61L 2209/15* (2013.01)

(58) Field of Classification Search
CPC .......... A61L 9/04; A61L 9/12; A61L 2209/11; A61L 2209/133; A61L 2209/15; A61L 9/127

See application file for complete search history.

(56) References Cited

U.S. PATENT DOCUMENTS 7,691,336 B2 * 4/2010 Westring ............. A01M 1/2033 422/123
11,796,126 B2 * 10/2023 Chao ......................... F16B 1/00
2002/0068010 A1 * 6/2002 Laudamiel-Pellet ... A61L 9/037 422/5
2013/0164178 A1 * 6/2013 Carmichael ............... A61L 9/04 422/123
2017/0197004 A1 * 7/2017 Kim ........................ A61L 9/035
2017/0259751 A1 * 9/2017 Gao .......................... A61L 9/12
2021/0361813 A1 * 11/2021 Ferreira .................... A61L 9/04
2022/0176064 A1 * 6/2022 Edwards ............... B05B 15/656
2024/0374774 A1 * 11/2024 Wu ........................... A61L 9/12
2025/0222154 A1 * 7/2025 Wu ........................... A61L 9/12

FOREIGN PATENT DOCUMENTS

KR 102357046 B1 1/2022
TW M646708 U 10/2023

* cited by examiner

*Primary Examiner* — Thomas P Burke
(74) *Attorney, Agent, or Firm* — METIS IP LLC

(57) ABSTRACT

A thin magnetic absorption fragrance device is mounted on a smartphone and includes a housing, a fragrance unit, a first upper cover, a first magnetic absorption unit and a lower cover. A first surface of the housing is concavely formed with a first accommodation recess, and the housing has a diffusion hole, an opening and a through hole. The opening fluidly communicates between the bottom of the first accommodation recess and a second surface of the housing. The through hole is formed through the housing to fluidly communicate between the first and the second surfaces. The diffusion hole fluidly communicates between the first accommodation recess and the through hole. The fragrance unit is mounted in the first accommodation recess. The first upper cover is mounted on the first surface. The first magnetic absorption unit is mounted in the housing. The lower cover is detachably mounted on the second surface.

14 Claims, 15 Drawing Sheets

THIN MAGNETIC ABSORPTION FRAGRANCE DEVICE

CROSS REFERENCE TO RELATED APPLICATIONS

The present application claims priority to Taiwan application No. 112213696, filed on Dec. 14, 2023, the content of which is hereby incorporated by reference in its entirety.

FIELD OF THE INVENTION

The present invention relates to a thin magnetic absorption fragrance device, especially a thin magnetic absorption fragrance device mounted on a smartphone.

BACKGROUND OF THE INVENTION

A conventional fragrance device applied on a mobile phone is magnetically absorbed on a metal casing of the mobile phone. That is, the conventional fragrance device is attached on a back of the mobile phone. Before a user puts the conventional fragrance device on the back of the mobile phone, fragrance essential oil needs to be dripped into a fragrance unit through a fragrance hole, so perfume smell will spread from the fragrance unit.

However, since there is no shelter between the fragrance hole of the fragrance unit and the mobile phone, the essential oils added by the user to the fragrance unit and a fragrance liquid volatilized by the fragrance unit will overflow through the fragrance hole and wet the metal casing on the back of the mobile phone. As a result, a paint or a coating of the metal casing will be discolored or peeled off.

In addition, the fragrance unit and a magnetic absorption unit are respectively arranged in an upper space and a lower space of the conventional fragrance device. The arrangement will result in a larger size for the conventional fragrance device, which is not conducive to thinning the conventional fragrance device. Therefore, when the conventional fragrance device is magnetically absorbed on the mobile phone, the conventional fragrance device with a bulky size affects the user's experience in operating the mobile phone.

Accordingly, how to provide a thin magnetic absorption fragrance device has become an urgent research topic.

SUMMARY OF THE INVENTION

The present invention provides a thin magnetic absorption fragrance device mounted on a smartphone with a wireless charging element.

The thin magnetic absorption fragrance device includes a housing, a fragrance unit, a first upper cover, a first magnetic absorption unit and a lower cover. A first surface of the housing is concavely formed with a first accommodation recess, and the housing has at least one opening and a through hole. The at least one opening is formed in a bottom of the first accommodation recess and formed through the bottom of the first accommodation recess to fluidly communicate between the bottom of the first accommodation recess and the second surface of the housing. The through hole is formed through the housing to fluidly communicate between the first surface and the second surface. Moreover, the at least one opening is located on an outer periphery of the through hole. The fragrance unit is mounted in the first accommodation recess and exposed to the second surface of the housing through the at least one opening. The first upper cover is mounted on the first surface. The first magnetic absorption unit is mounted in the housing and located on an outer periphery of the first accommodation recess. The lower cover is detachably mounted on the second surface to cover the at least one opening.

The thin magnetic absorption fragrance device of the present invention is convenient for users to easily and quickly put it on their own smartphones, and can diffuse perfume smells through various fragrance units to give users a refresher. The present invention also has advantages of low cost, fragrant smell, and long-lasting effect. Moreover, the thin magnetic absorption fragrance device can be attracted to an electrical device through the first magnetic absorption unit.

DETAILED DESCRIPTION OF THE INVENTION

Figure 1A:
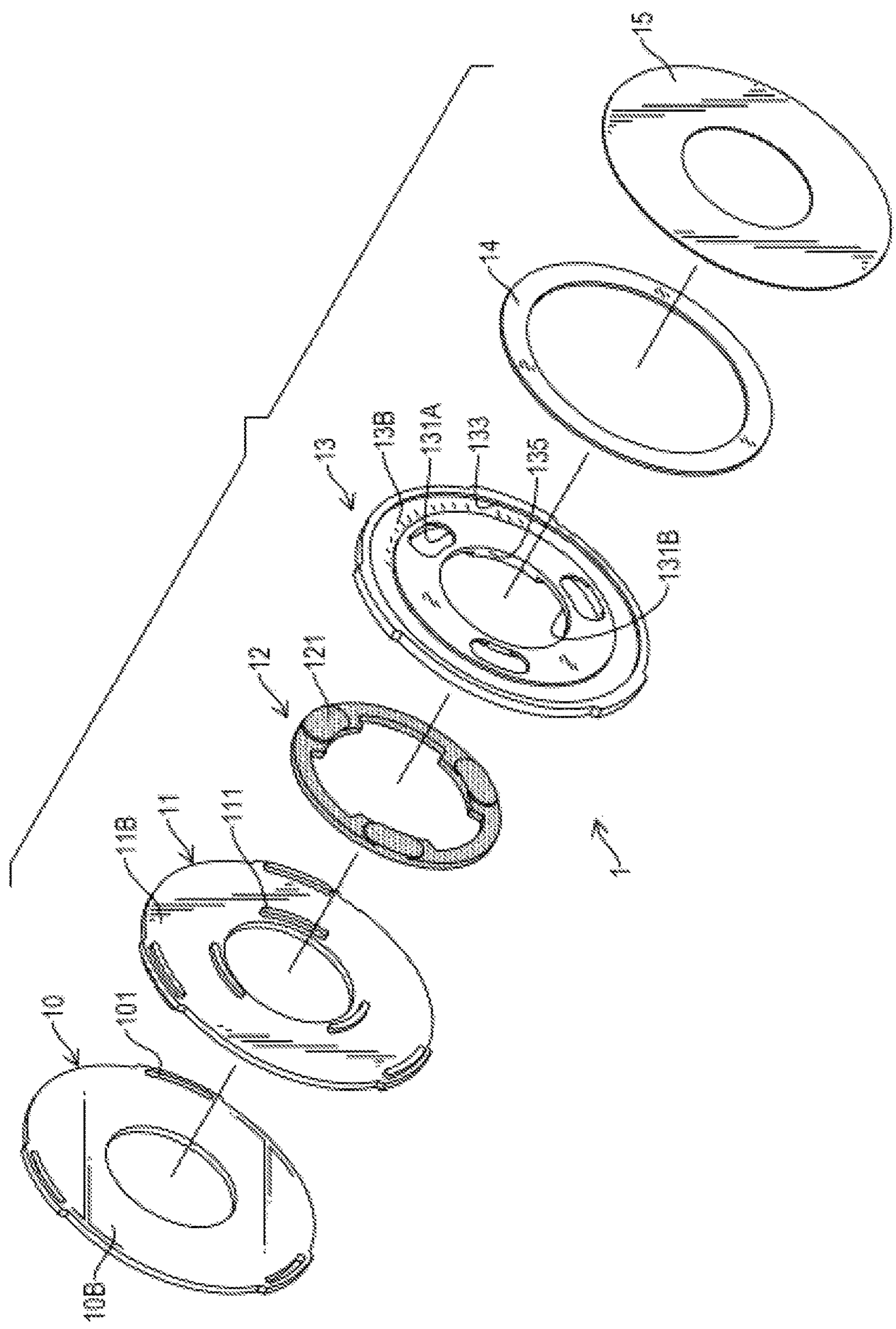
FIG. 1A is a first exploded view of a first embodiment of a thin magnetic absorption fragrance device in accordance with the present invention.
Figure 1B:
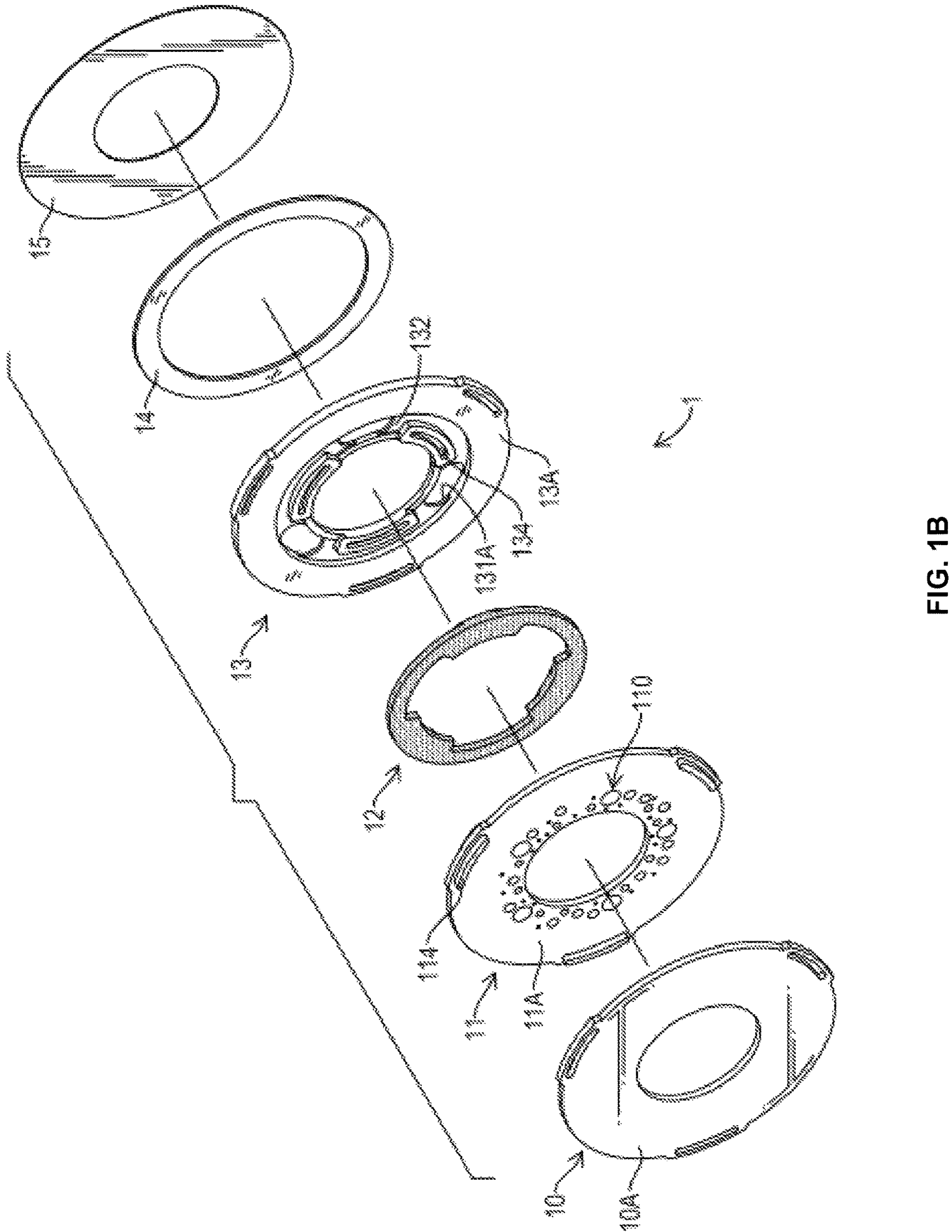
FIG. 1B is a second exploded view of the first embodiment of the thin magnetic absorption fragrance device of the present invention.
Figure 1C:
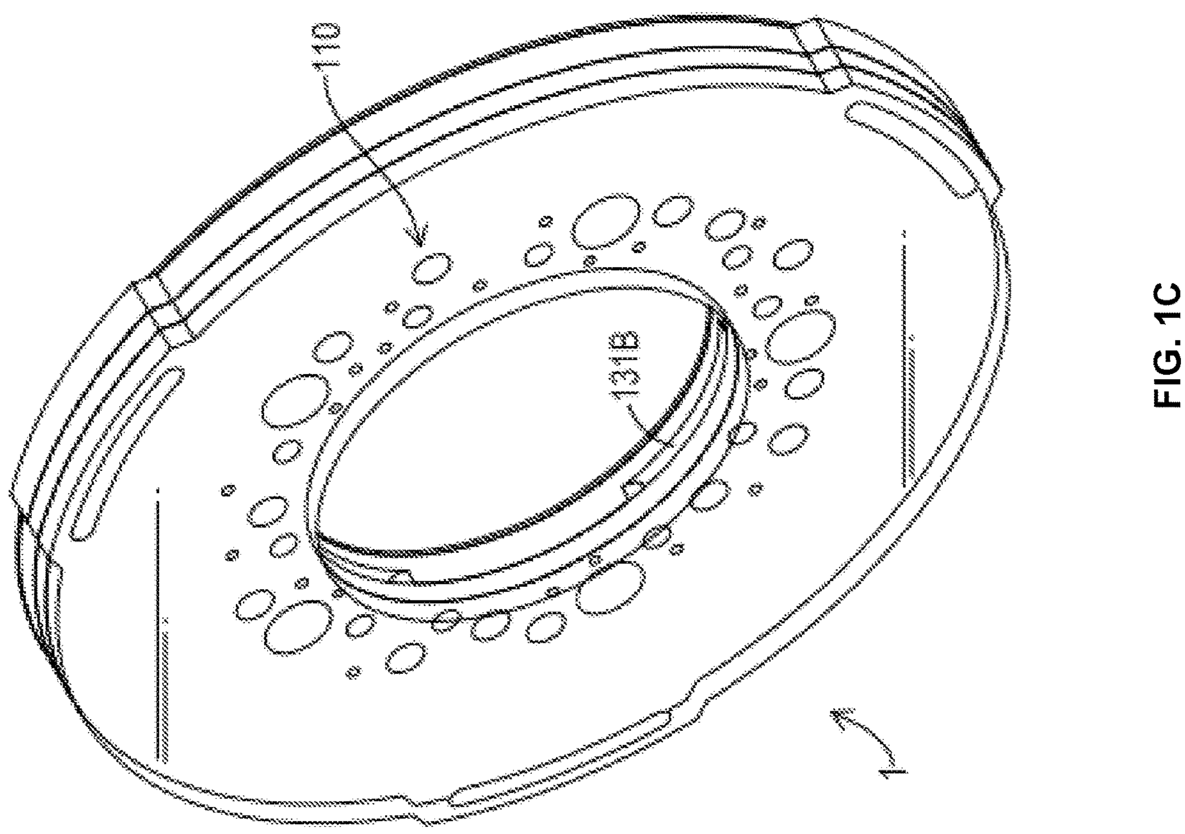
FIG. 1C is a perspective view of the first embodiment of the thin magnetic absorption fragrance device of the present invention.
Figure 1D:
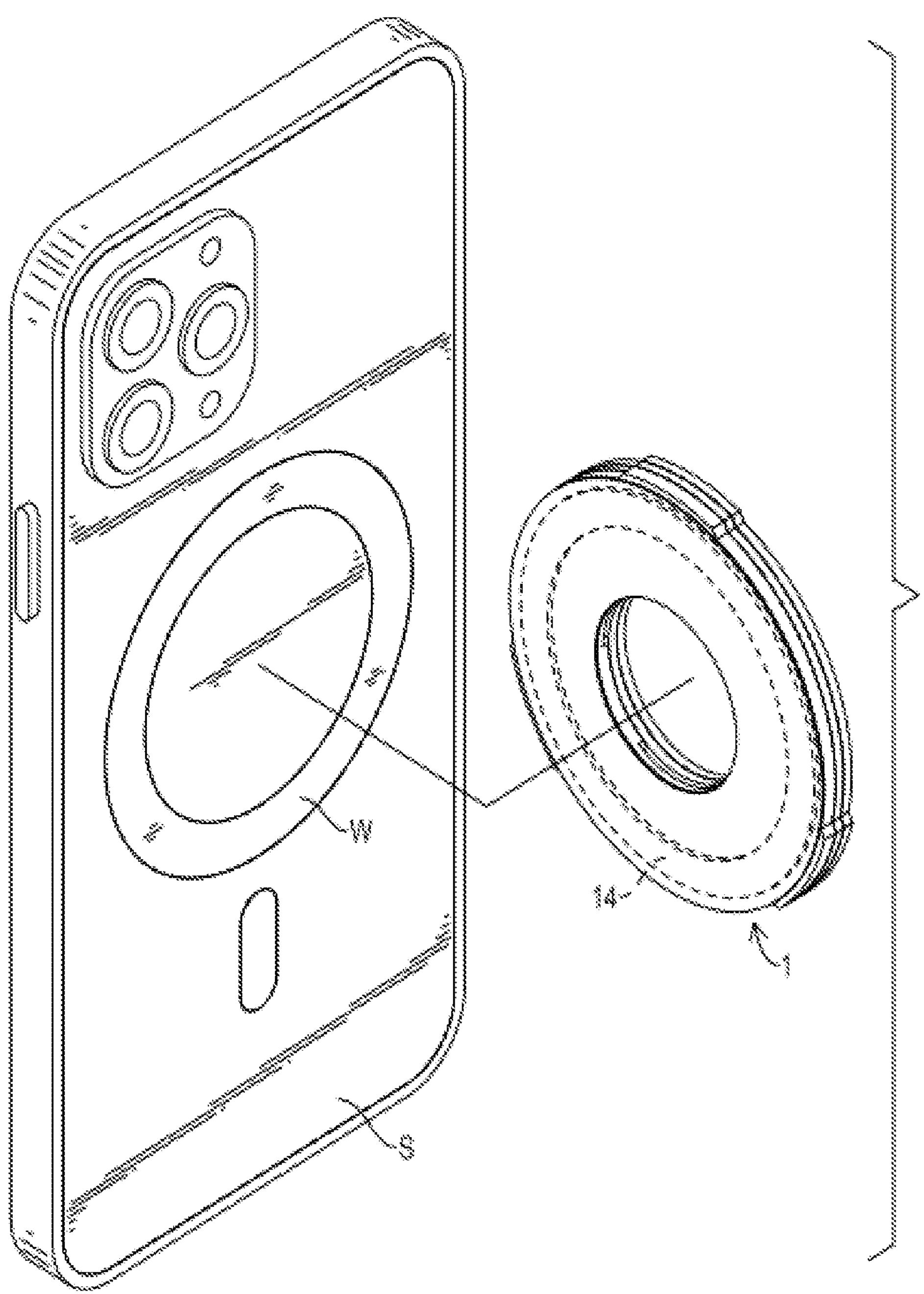
FIG. 1D is a schematic diagram of applications of the thin magnetic absorption fragrance device of the present invention.
Figure 1E:
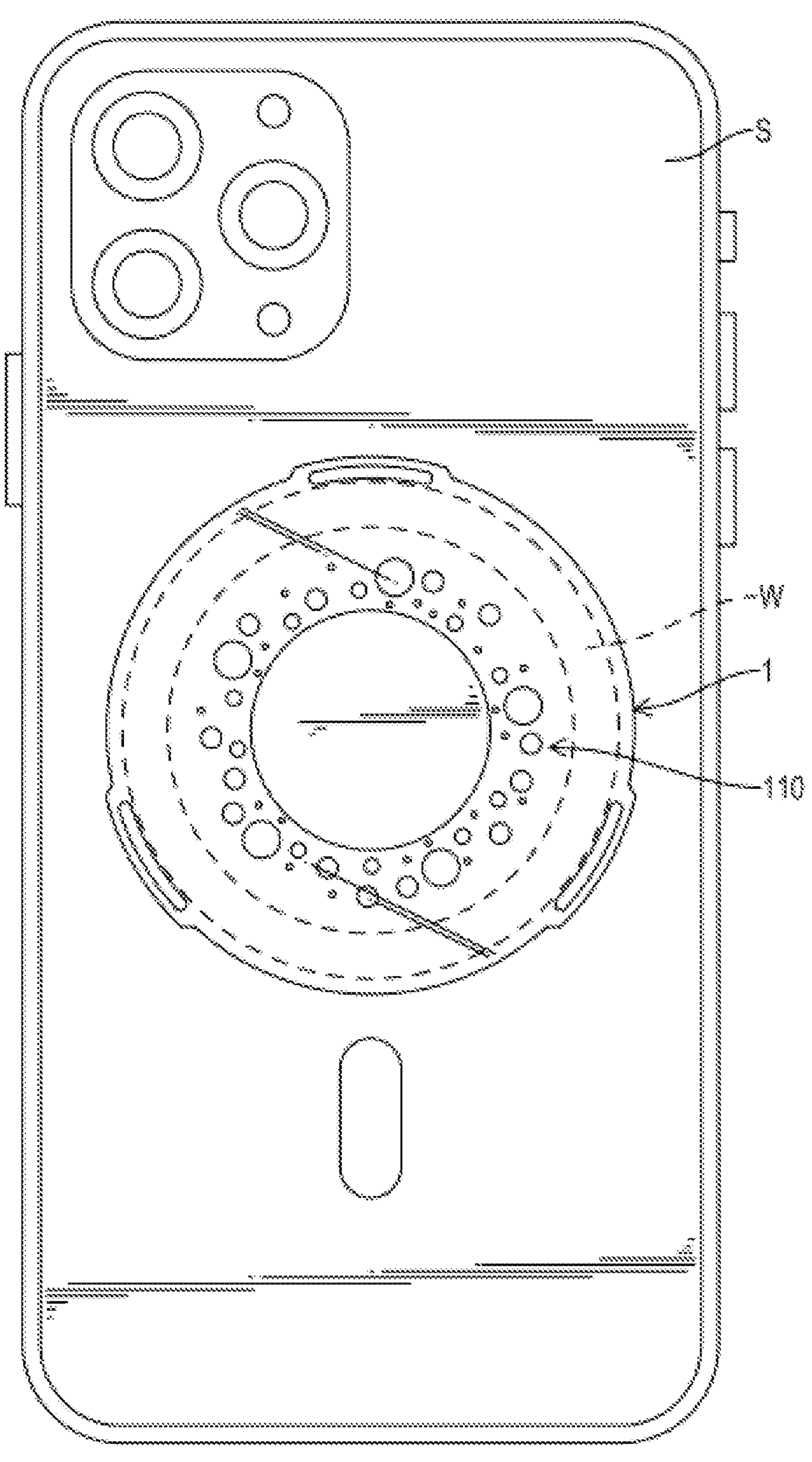
FIG. 1E is a schematic diagram of applications of the thin magnetic absorption fragrance device of the present invention.
Figure 1F:
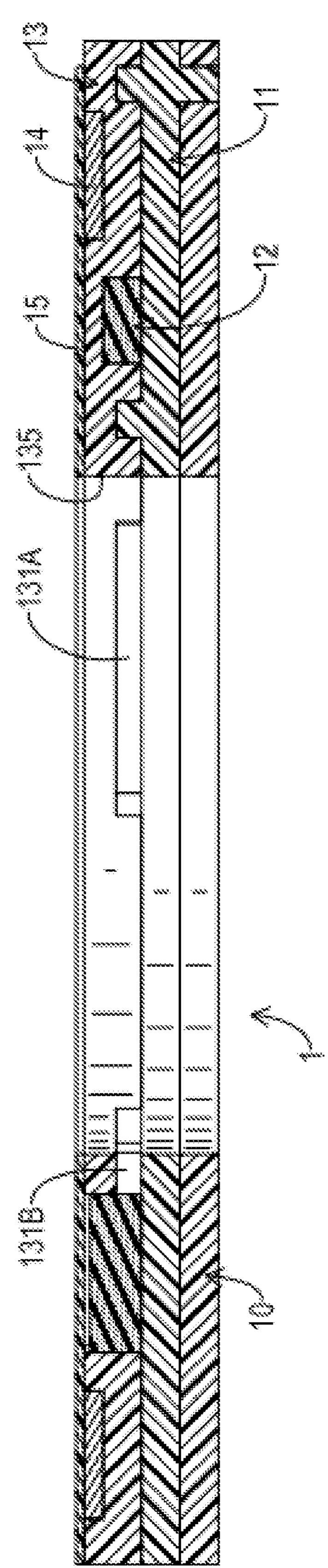
FIG. 1F is a cross-sectional view of the thin magnetic absorption fragrance device of the present invention.

With reference to FIGS. 1A to IF, FIGS. 1A to IC are a first exploded view, a second exploded view, and a perspective view of a first embodiment of a thin magnetic absorption fragrance device 1 in accordance with the present invention, FIGS. 1D to 1E are schematic views of applications of the thin magnetic absorption fragrance device, and FIG. 1F is a cross-sectional view of the thin magnetic absorption fragrance device. The thin magnetic absorption fragrance device 1 is mounted on a smartphone S with a wireless charging element W, and includes a first upper cover 11, a fragrance unit 12, a housing 13, a first magnetic absorption unit 14, and a lower cover 15.

The housing 13 has a first surface 13A and a second surface 13B opposite to each other, and the first surface 13A is concavely formed with a first accommodation recess 132. Furthermore, the housing 13 has at least one diffusion hole 131B, at least one opening 131A, and a through hole 135. The at least one opening 131A is formed in a bottom of the first accommodation recess 132 and formed through the bottom of the first accommodation recess 132 to fluidly communicate between the bottom of the first accommodation recess 132 and the second surface 13B. The through hole 135 is formed through the housing 13 to fluidly communicate between the first surface 13A and the second surface 13B, and the at least one opening 131A is located on an outer periphery of the through hole 135, and the through hole 135 is located on an inner periphery of the first accommodation recess 132. The at least one diffusion hole 131B is formed on a recess wall of the first accommodation recess 132 and formed through the recess wall to fluidly communicate between the first accommodation recess 132 with the through hole 135.

The fragrance unit 12 is mounted in the first accommodation recess 132 of the housing 13 and exposed to the second surface 13B of the housing 13 through the at least one opening 131A. The first upper cover 11 is mounted on the first surface 13A of the housing 13. The first magnetic absorption unit 14 is mounted in the housing 13 and located on an outer periphery of the first accommodation recess 132. The lower cover 15 is detachably mounted on the second surface 13B of the housing 13 to cover at least one opening 131A.

The first upper cover 11 has a first surface 11A and a second surface 11B opposite to each other. The second surface 11B of the first upper cover 11 faces the first surface 13A of the housing 13, and the second surface 11B of the first upper cover 11 is mounted on the fragrance unit 12 and is connected to the first surface 13A of the housing 13. The first magnetic absorption unit 14 is mounted in a second accommodation recess 133 of the housing 13, and is located on the outer periphery of the at least one opening 131A. The lower cover 15 is mounted on the second surface 13B of the housing 13. The lower cover 15 covers the at least one opening 131A and is connected to the second surface 13B of the housing 13. In addition, the first surface 11A of the first upper cover 11 is a surface facing the user. Therefore, various patterns can be set on the first surface 11A of the first upper cover 11 according to user needs.

The second surface 11B of the first upper cover 11 includes at least one first combining portion 111, the first surface 13A of the housing 13 includes at least one second combining portion 134, and the at least one first combining portion 111 is connected to the at least one second combining portion 134 correspondingly. In an embodiment of the present invention, the first combining portion 111 and the second combining portion 134 include corresponding concave and convex structures. Alternatively, in other embodiments, the first upper cover 11 and the housing 13 are connected by thermal fusion without connecting via the first combining portion 111 and the second combining portion 134.

The thin magnetic absorption fragrance device 1 further includes a second upper cover 10. The second upper cover 10 has a first surface 10A and a second surface 10B opposite to each other. The second surface 10B of the second upper cover 10 faces the first surface 11A of the first upper cover 11. At least one third combining portion 101 is formed on the second surface 10B of the second upper cover 10. At least one fourth combining portion 114 is formed on the first surface 11A of the first upper cover 11. The at least one third combining portion 101 is connected to the fourth combining portion 114 correspondingly.

The thin magnetic absorption fragrance device 1 further includes a pattern 110 as shown in FIG. 1B, and the pattern 110 is arranged on the second surface 10B of the second upper cover 10 or mounted on the first surface 11A of the first upper cover 11. Additionally, the second upper cover 10 is a transparent cover.

Following the above, in addition to being mounted on the first accommodation recess 132, the fragrance unit 12 is further exposed in the at least one opening 131A and the at least one diffusion hole 131B, so that the fragrance unit 12 diffuses fragrance through the diffusion hole 131B. Furthermore, the fragrance unit 12 includes materials such as paper, bamboo, rattan branches, gypsum, ceramics, diatomaceous earth, wood, cloth, lava, crystal, etc. The fragrance unit 12 has at least one protruding portion 121, and the at least one protruding portion 121 is mounted in the at least one opening 131A of the housing 13. Therefore, the at least one protruding portion 121 is exposed to the second surface 13B of the housing 13 through the at least one opening 131A.

The housing 13 includes the through hole 135. The through hole 135 is formed through the first surface 13A and the second surface 13B of the housing 13, and fluidly communicates to the at least one diffusion hole 131B. Therefore, when the fragrance unit 12 is covered by the first upper cover 11 and the lower cover 15, the thin magnetic absorption fragrance device 1 can diffuse fragrance of the fragrance unit 12 via the diffusion hole 131B. In addition, the at least one opening 131A is formed on the periphery of the through hole 135. Actually, the first upper cover 11, the fragrance unit 12, the housing 13, the first magnetic absorption unit 14, and the lower cover 15 each have a corresponding through hole to correspond to a pattern arranged on the back of the smartphone S from the iPhone® series of Apple Inc. Furthermore, the thin magnetic absorption fragrance device 1 of the present invention is mainly applied to mount on the smartphone S, such as the smartphone S of the iPhone® series of Apple Inc., and the smartphone S of the iPhone® series of Apple Inc. has a pattern on the back of the smartphone S. In order to avoid the thin magnetic absorption fragrance device 1 covering the pattern when the thin magnetic absorption fragrance device 1 is mounted on the back of the smartphone S, the first upper cover 11, the fragrance unit 12, the housing 13, the first magnetic absorption unit 14, and the lower cover 15 have the through holes corresponding to the pattern on the back of the smartphone S in location. Therefore, when the user is operating the present invention to diffuse fragrance, the user still can see the pattern of Apple Inc.

Following the above, the second surface 13B of the housing 13 is concavely formed with the second accommodation recess 133. The second accommodation recess 133 is staggered with the first accommodation recess 132, and the second accommodation recess 132 is located on the outer periphery of the first accommodation recess 132. Wherein, the first magnetic absorption unit 14 is mounted in the second accommodation recess 133 of the housing 13, and the fragrance unit 12 is mounted in the first accommodation recess 132 of the housing 13.

The first magnetic absorption unit 14 is mounted in the second accommodation recess 133 of the housing 13 in an adhesive way. In an embodiment of the present invention, the first magnetic absorption unit 14 is annular in shape and corresponds in location to the wireless charging element W mounted on the back of the smartphone S to adsorb on the wireless charging element W.

In an embodiment of the present invention, the lower cover 15 is a second magnetic absorption unit with magnetism. The second magnetic absorption unit is embedded in the second accommodation recess 133 and is arranged corresponding in location to the first magnetic absorption unit 14, so that the second magnetic absorption unit contacts and is adsorbed to the first magnetic absorption unit 14 mounted in the second accommodation recess 133. That is, a sum of a thickness of the first magnetic absorption unit 14 and a thickness of the stacked lower cover 15 is equal to a depth of the second accommodation recess 133 in the housing 13. Accordingly, an overall thickness of the thin magnetic absorption fragrance device 1 can be reduced through this arrangement, and a surface of the thin magnetic absorption fragrance device 1 can be a flat surface when the thin magnetic absorption fragrance device 1 is attached to the back of the smartphone S.

In another embodiment of the present invention, the lower cover 15 can be also mounted on the second surface 13B of the housing 13, that is, the lower cover 15 is mounted on a recess wall of the second accommodation recess 133. A difference from the above embodiment is that in the embodiment, the lower cover 15 is not buried or embedded in the second accommodation recess 133 of the housing 13. However, because the lower cover 15 has a relatively thin thickness, the thickness of the lower cover 15 does not affect the overall thickness of the thin magnetic absorption fragrance device 1.

Figure 2:
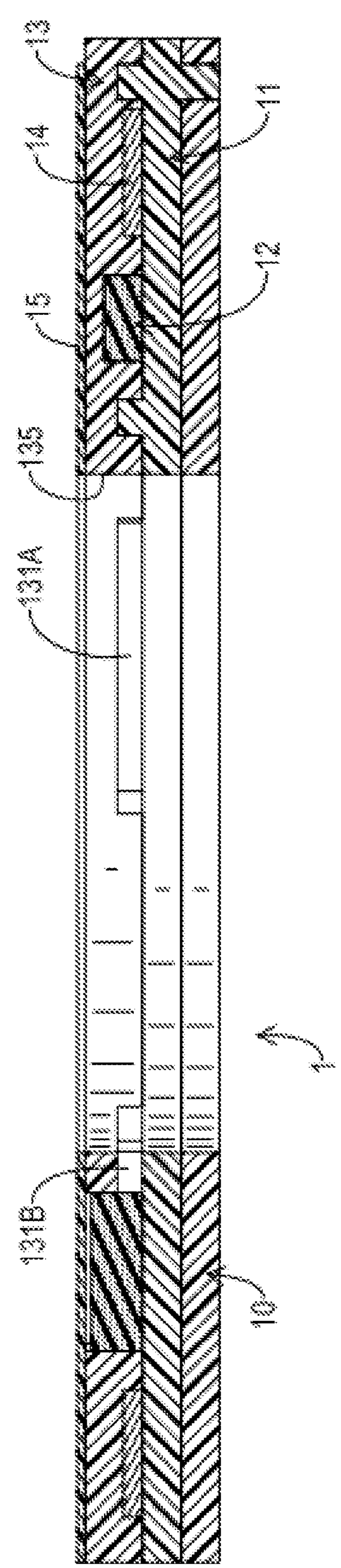
FIG. 2 is a cross-sectional view of a second embodiment of the thin magnetic absorption fragrance device in accordance with the present invention.

Referring to FIG. 2, FIG. 2 is a cross-sectional view of a second embodiment of the thin magnetic absorption fragrance device 1 of the present invention. In the second embodiment, the fragrance unit 12 and the first magnetic absorption unit 14 are mounted on the same surface of the horsing 13. In particular, the first surface 13A of the housing 13 is concavely formed with the second accommodation recess 133 in the second embodiment. The second accommodation recess 133 is staggered with the first accommodation recess 132, the second accommodation recess 132 is located on the outer periphery of the first accommodation recess 132, and the first magnetic absorption unit 14 is mounted in the second accommodation recess 133 of the housing 13.

Figure 3:
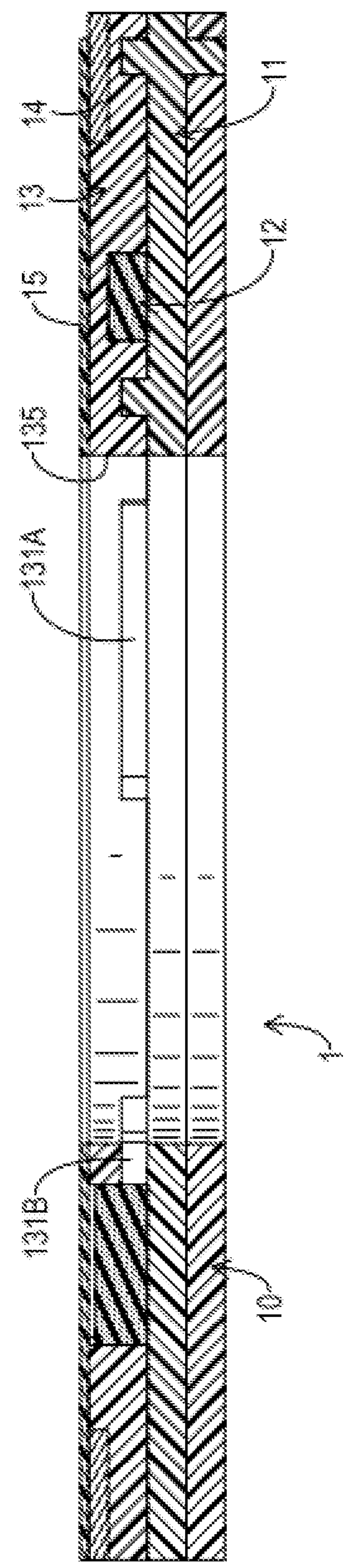
FIG. 3 is a cross-sectional view of a third embodiment of the thin magnetic absorption fragrance device in accordance with the present invention.

Referring to FIG. 3, FIG. 3 is a cross-sectional view of a third embodiment of the thin magnetic absorption fragrance device 1 of the present invention. In the third embodiment, the fragrance unit 12 and the first magnetic absorption unit 14 are mounted on different surfaces of the housing 13.

Figure 4:
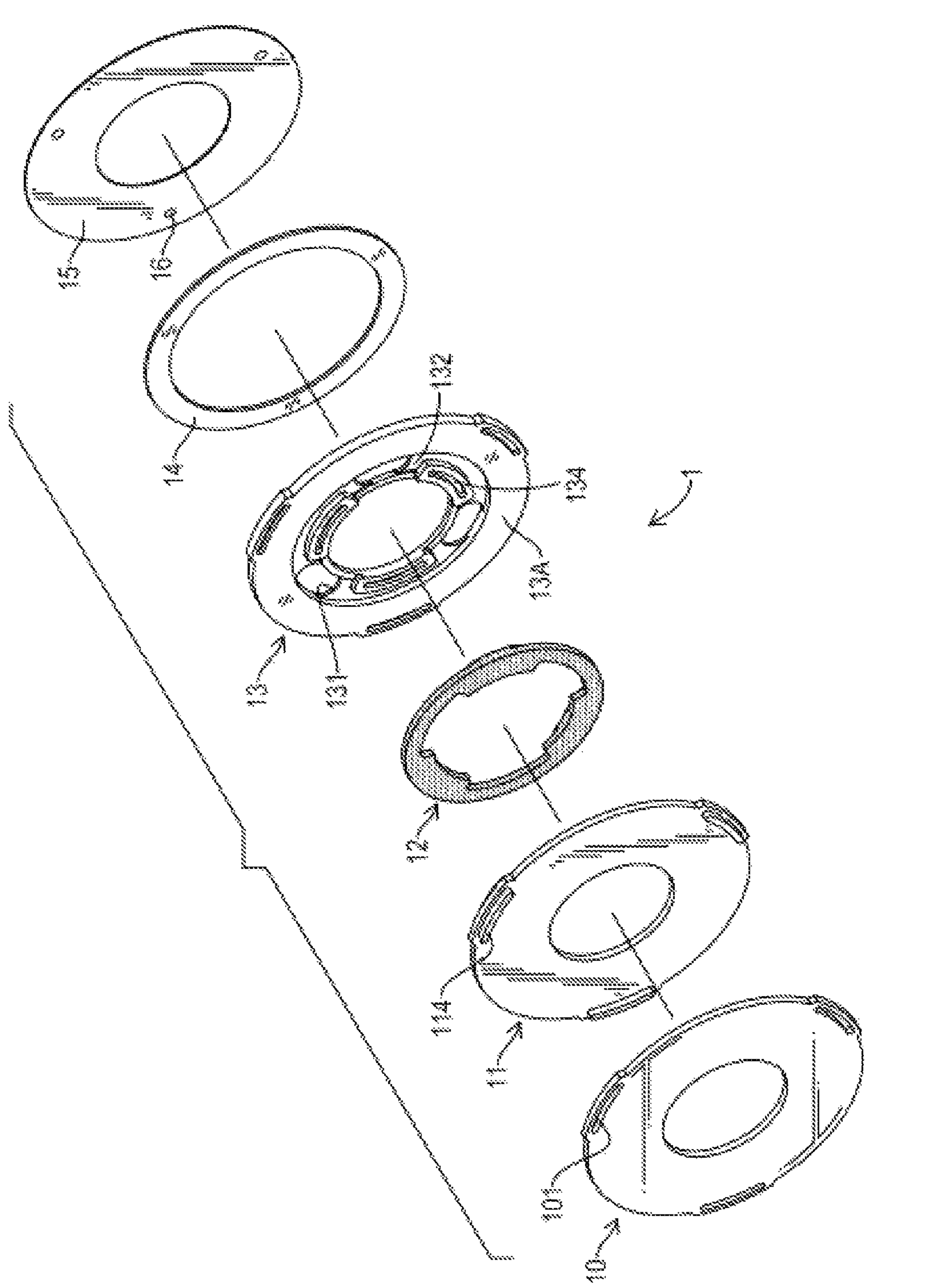
FIG. 4 is an exploded view of a fourth embodiment of the thin magnetic absorption fragrance device in accordance with the present invention.

Referring to FIG. 4, FIG. 4 is an exploded view of a fourth embodiment of the thin magnetic absorption fragrance device 1 of the present invention. A difference between the fourth embodiment and the first embodiment above mentioned is that the lower cover 15 of the fourth embodiment is not a magnetic unit. In the fourth embodiment, a second magnetic absorption unit 16 is embedded in the lower cover 15, and the second magnetic absorption unit 16 is mounted corresponding to in position to the first magnetic absorption unit 14 and corresponding in position to the wireless charging element W in the back of the smartphone S. The upper cover 15 can simultaneously adsorb the first magnetic absorption unit 14 and the wireless charging element W through the second magnetic absorption unit 16, and functions of the remaining components are same as those of the components in the above embodiments and will not be repeated.

Referring to FIGS. 5A to 5D, which are a first exploded view, a second exploded view, a top view, and a cross-sectional view of a fifth embodiment of the thin magnetic absorption fragrance device 1 of the present invention. A difference between the fifth embodiment and the above-mentioned embodiments is that the housing 13 of the thin magnetic absorption fragrance device 1 of the fifth embodiment further has a third accommodation recess 136 and a first groove 137. The third accommodation recess 136 is formed concavely on the second surface 13B. The first groove 137 is formed in the third accommodation recess 136, and the third accommodation recess 136 is disposed on an inner periphery of the second accommodation recess 133. The first magnetic absorption unit 14 is mounted in the second accommodation recess 133, and a third magnetic absorption unit 181 is mounted in the first groove 137.

A lower cover 17 is mounted in the third accommodation recess 136 and has a first surface 17A and a second surface 17B opposite to each other. The first surface 17A of the lower cover 17 faces the second surface 13B of the housing 13, and the first surface 17A of the lower cover 17 is mounted with at least one fourth magnetic absorption unit 182. At least one second groove 171 is formed on the first surface 17A of the lower cover 17 and corresponding to the first groove 137, and the at least one fourth magnetic absorption unit 182 is embedded in the second groove 171 to adsorb and mount on the third magnetic absorption unit 181. The housing 13 is attracted to the lower cover 17 through the third magnetic absorption unit 181 and the fourth magnetic absorption unit 182, and is attracted to the wireless charging element W by the first magnetic absorption unit 14. Functions of the remaining components are same as those of the components in the above embodiments and will not be repeated.

Figure 5A:
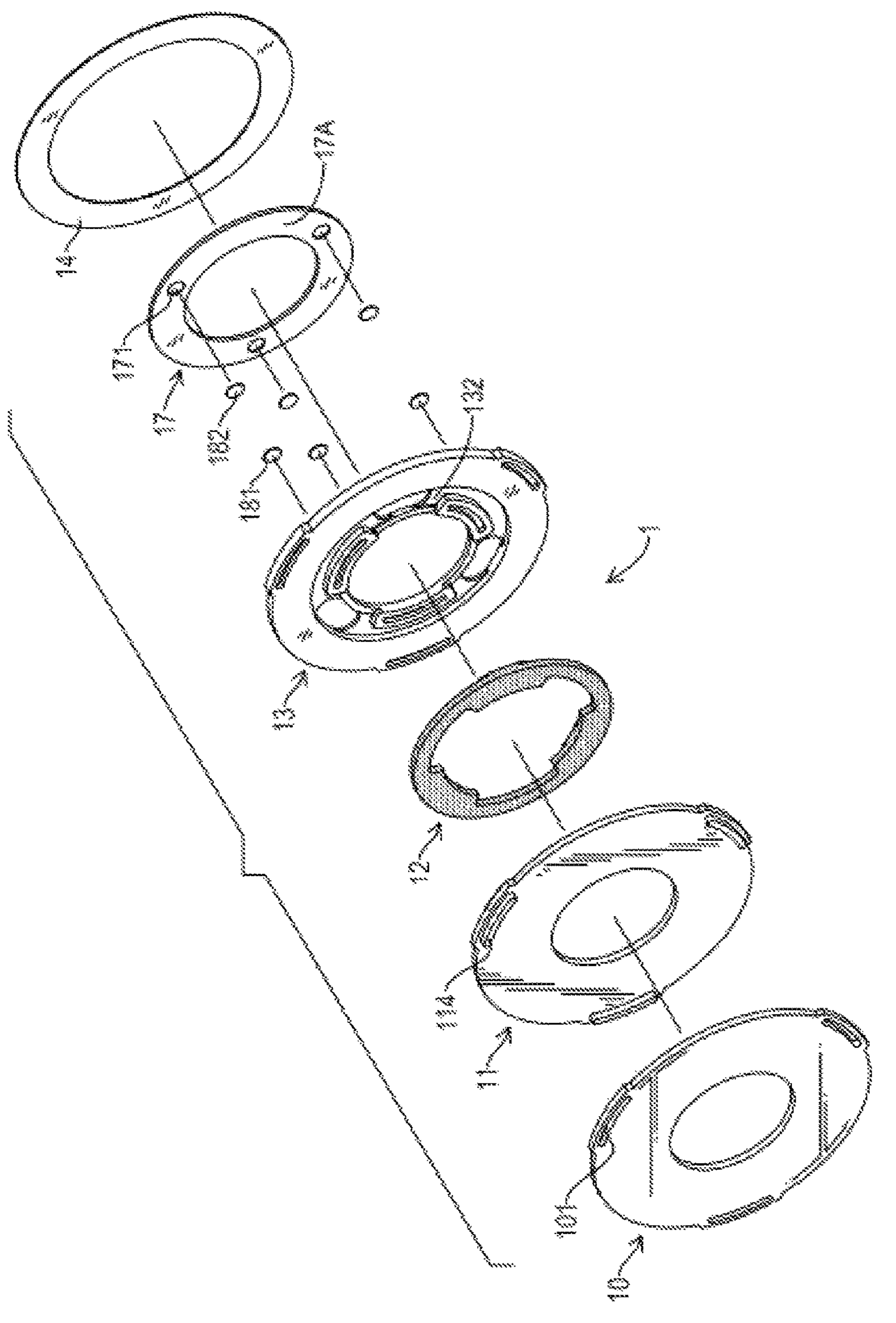
FIG. 5A is a first exploded view of a fifth embodiment of the thin magnetic absorption fragrance device in accordance with the present invention.
Figure 5B:
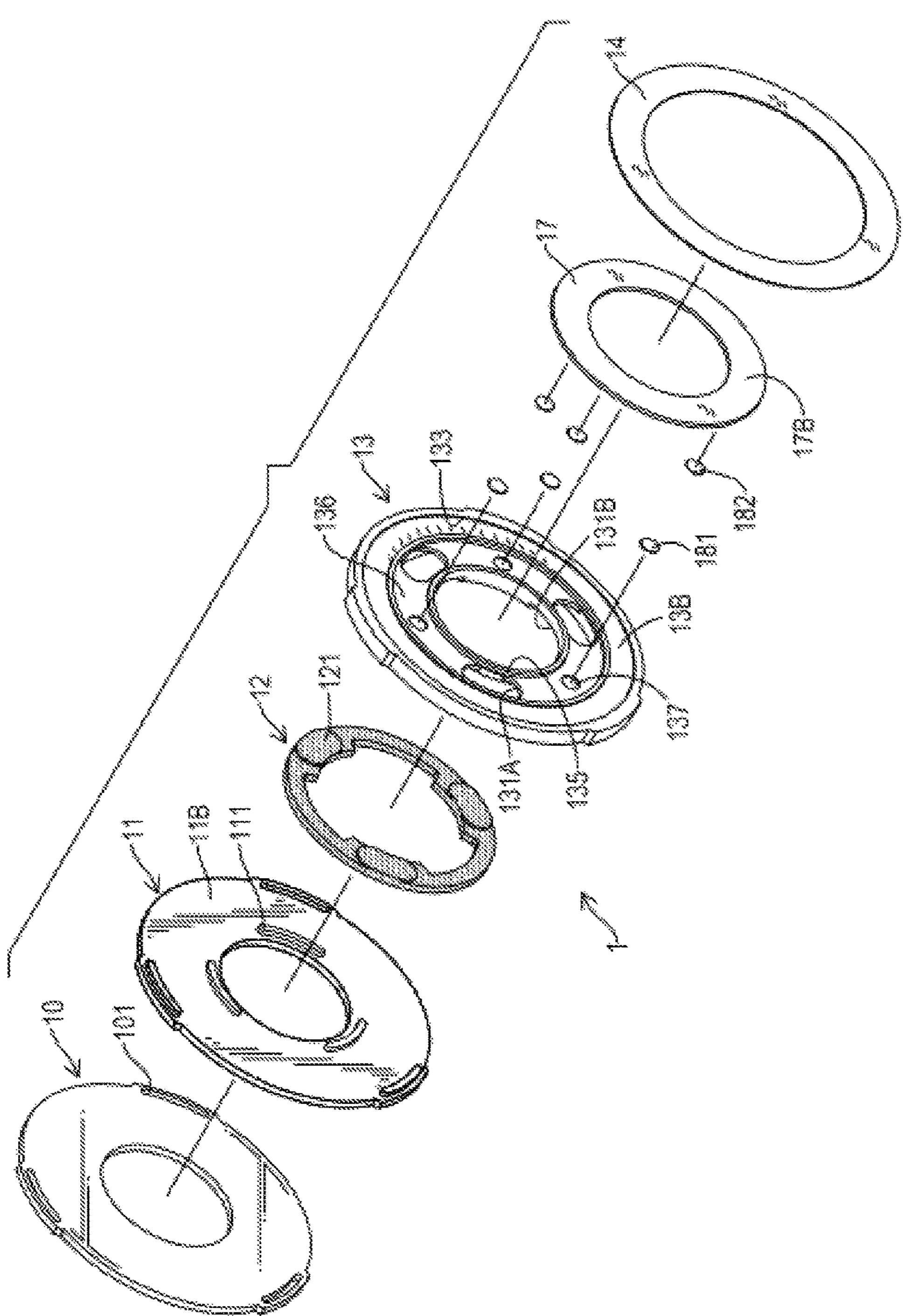
FIG. 5B is a second exploded view of the fifth embodiment of the thin magnetic absorption fragrance device of the present invention.
Figure 5C:
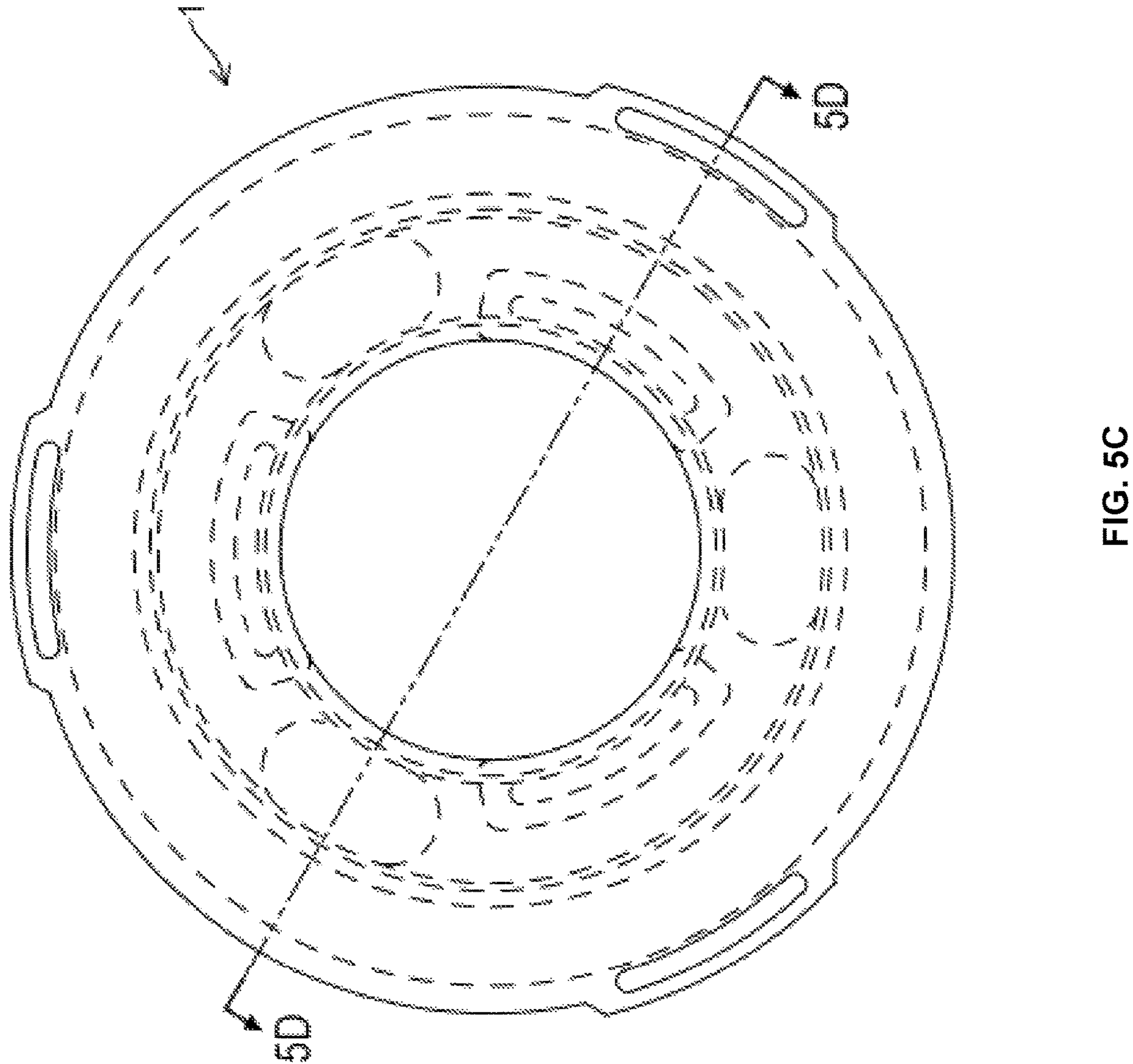
FIG. 5C is a top view of the fifth embodiment of the thin magnetic absorption fragrance device of the present invention.
Figure 5D:
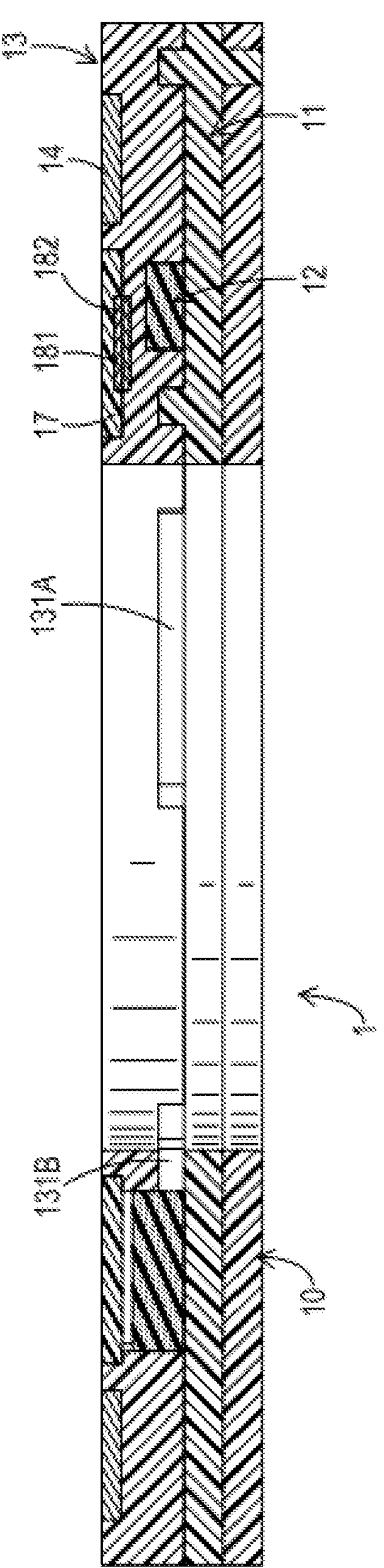
FIG. 5D is a cross-sectional view of the fifth embodiment of the thin magnetic absorption fragrance device of the present invention.

Continuing from the above, in another embodiment of the thin magnetic absorption fragrance device 1 shown in FIGS. 5A and 5B, when the lower cover 17 is made of a magnetic material, the lower cover 17 cannot be mounted with the fourth magnetic absorption unit 182. That is, the lower cover 17 uses its own magnetism to attract the third magnetic absorption unit 181 in the first groove 137.

Figure 6:
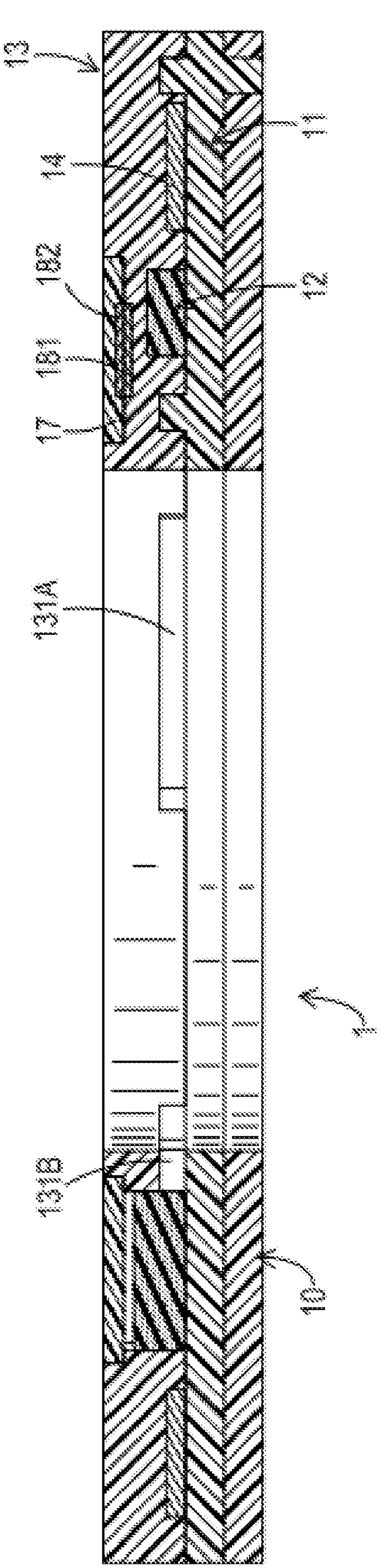
FIG. 6 is a cross-sectional view of a sixth embodiment of the thin magnetic absorption fragrance device in accordance with the present invention.

Referring to FIG. 6, FIG. 6 is a cross-sectional view of a sixth embodiment of the thin magnetic absorption fragrance device 1 of the present invention. In the sixth embodiment, the fragrance unit 12 and the first magnetic absorption unit 14 are mounted on the same surface of the housing 13.

Figure 7:
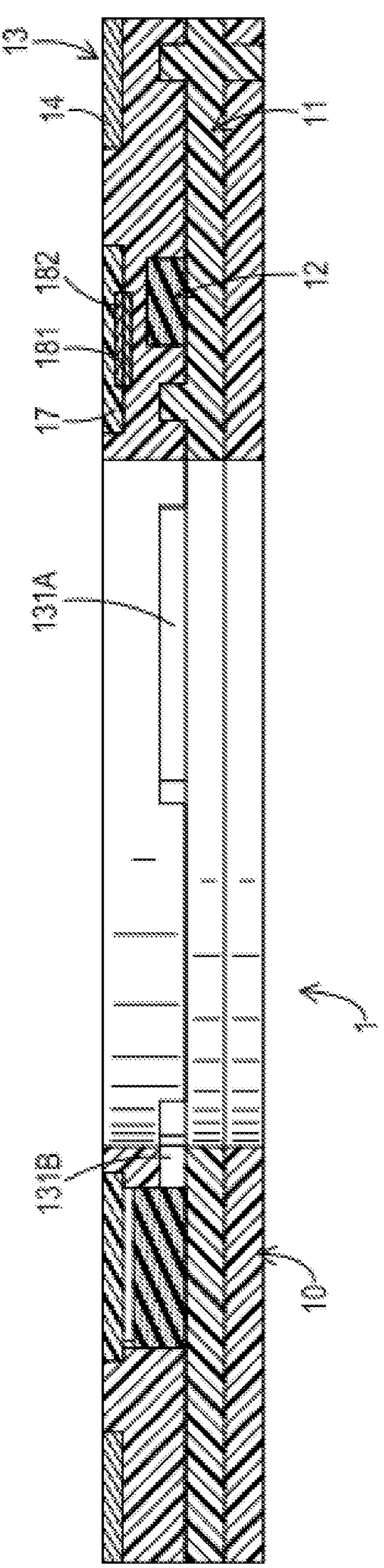
FIG. 7 is a cross-sectional view of a seventh embodiment of the thin magnetic absorption fragrance device in accordance with the present invention.

Referring to FIG. 7, FIG. 7 is a cross-sectional view of a seventh embodiment of the thin magnetic absorption fragrance device 1 of the present invention. In the seventh embodiment, the first magnetic absorption unit 14 is exposed to an outer edge of the housing 13.

In view of the above, the thin magnetic absorption fragrance device 1 of the present invention is convenient for users to easily and quickly set it up on their own smartphones S, and can diffuse fragrance through various fragrance units 12 to give users a refresher. The present invention also has advantages of low cost, fragrant smell, and long-lasting effect. Moreover, the thin magnetic absorption fragrance device 1 can attract to an electrical device through the first magnetic absorption unit 14.

What is claimed is:

1. A magnetic absorption fragrance device, adapted to be mounted on a smartphone with a wireless charging element, and comprising:
- a housing comprising:
  - a first accommodation recess concavely formed on a first surface;
  - a second surface opposite to the first surface;
  - at least one opening formed in a bottom of the first accommodation recess and formed through the bottom of the first accommodation recess to fluidly communicate between the bottom of the first accommodation recess and the second surface;
  - a through hole formed through the housing to fluidly communicate between the first surface and the second surface, wherein the at least one opening is located on an outer periphery of the through hole, and the through hole is located on an inner periphery of the first accommodation recess;
  - at least one diffusion hole formed on a recess wall of the first accommodation recess and formed through the recess wall to fluidly communicate with the first accommodation recess and the through hole;
- a fragrance unit mounted in the first accommodation recess of the housing, and exposed to the second surface of the housing through the at least one opening;
- a first upper cover mounted on the first surface of the housing;
- a first magnetic absorption unit mounted in the housing and located on an outer periphery of the first accommodation recess; and
- a lower cover detachably mounted on the second surface of the housing to cover the at least one opening.

2. The magnetic absorption fragrance device as claimed in claim 1, wherein
- a second accommodation recess is concavely formed on the second surface of the housing and is staggered with the first accommodation recess;
- the second accommodation recess is located on the outer periphery of the first accommodation recess; and
- the first magnetic absorption unit is mounted in the second accommodation recess of the housing.

3. The magnetic absorption fragrance device as claimed in claim 1, wherein
- a second accommodation recess is concavely formed on the first surface of the housing and is staggered with the first accommodation recess;
- the second accommodation recess is located on the outer periphery of the first accommodation recess; and
- the fragrance unit is mounted in the first accommodation recess of the housing.

4. The magnetic absorption fragrance device as claimed in claim 1, wherein the lower cover includes at least one second magnetic absorption unit disposed corresponding to the first magnetic absorption unit in position.

5. The magnetic absorption fragrance device as claimed in claim 1, wherein the fragrance unit has at least one protruding portion, and the at least one protruding portion is embedded in the at least one opening and exposed to the second surface through the at least one opening.

6. The magnetic absorption fragrance device as claimed in claim 1, wherein
- the first upper cover has a first surface and a second surface opposite to each other, and the second surface of the first upper cover faces the first surface of the housing;
- the second surface of the first upper cover is formed with at least one first combining portion;
- the first surface of the housing is formed with at least one second combining portion; and
- the at least one first combining portion is connected to the at least one second combining portion.

7. The magnetic absorption fragrance device as claimed in claim 6, wherein the magnetic absorption fragrance device includes a second upper cover;
- the second upper cover has a first surface and a second surface opposite to each other, and the second surface of the second upper cover faces the first surface of the first upper cover;
- the second surface of the second upper cover is formed with at least one third combining portion;
- the first surface of the first upper cover is formed with at least one fourth combining portion; and
- the at least one third combining portion is connected to the fourth combining portion.

8. The magnetic absorption fragrance device as claimed in claim 7, wherein
- the magnetic absorption fragrance device includes a pattern arranged on the first surface of the first upper cover; and
- the second upper cover is a transparent cover.

9. The magnetic absorption fragrance device as claimed in claim 1, wherein a second accommodation recess is concavely formed on the second surface of the housing; the lower cover includes at least one second magnetic absorption unit; a third accommodation recess is formed concavely on the second surface of the housing;
- at least one third magnetic absorption unit is mounted in a bottom of the third accommodation recess;
- the lower cover is mounted in the third accommodation recess and has a first surface and a second surface opposite to each other, the first surface of the lower cover faces the second surface of the housing, and the first surface of the lower cover is mounted with at least one fourth magnetic absorption unit; and
- the at least one third magnetic absorption unit is disposed corresponding to the fourth magnetic absorption unit in position.

10. The magnetic absorption fragrance device as claimed in claim 1, wherein
- a second accommodation recess is concavely formed on the second surface of the housing; the lower cover includes at least one second magnetic absorption unit; a third accommodation recess is formed concavely on the second surface of the housing;
- at least one third magnetic absorption unit is mounted in a bottom of the third accommodation recess;
- the lower cover is mounted in the third accommodation recess and has a first surface and a second surface opposite to each other, and the first surface of the lower cover faces the second surface of the housing; and
- the lower cover is made of a magnetic material.

11. The magnetic absorption fragrance device as claimed in claim 4, wherein the second magnetic absorption unit is embedded in the lower cover.

12. The magnetic absorption fragrance device as claimed in claim 11, wherein the second magnetic absorption unit is mounted corresponding in position to the first magnetic absorption unit and corresponding in position to a wireless charging element on a back of a smartphone.

13. The magnetic absorption fragrance device as claimed in claim 12, wherein the upper cover simultaneously adsorbs the first magnetic absorption unit and the wireless charging element through the second magnetic absorption unit.

14. The magnetic absorption fragrance device as claimed in claim 4, wherein the lower cover is not a magnetic unit.

* * * * *